US00PP07988P

United States Patent [19]

Strahle

[11] Patent Number: Plant 7,988

[45] Date of Patent: Sep. 29, 1992

[54] FLORIBUNDA ROSE PLANT CARALE

[75] Inventor: Robert Strahle, Carlton, Oreg.

[73] Assignee: Carlton Rose Nurseries, Inc., Carlton, Oreg.

[21] Appl. No.: 619,562

[22] Filed: Nov. 29, 1990

[51] Int. Cl.[5] ..... A01H 5/00

[52] U.S. Cl. ..... Plt./15

[58] Field of Search ..... Plt./15, 24

*Primary Examiner*—James R. Feyrer

*Attorney, Agent, or Firm*—Chernoff, Vilhauer, McClung & Stenzel

[57] ABSTRACT

A vigorous rose plant of the floribunda class obtained as a seedling from a seed parent entitled "Escort" and a pollen parent entitled "Golden Nugget" provides abundant long-lasting solid yellow flowers which maintain their true color from flower opening through petal drop on a continuous basis when grown in a greenhouse.

1 Drawing Sheet

BACKGROUND AND SUMMARY OF THE INVENTION

The present invention relates to a new and distinct variety of floribunda rose plant, a seedling resulting from a definite effort to produce an improvement of this class of rose. The object of the present invention is to provide a rose plant of the floribunda class which is capable of freely yielding quality-cut flowers under greenhouse conditions.

The primary features of this new variety which connotates its distinctive advance over previously existing types is its ability to produce an abundance of solid yellow flowers which remain true after being cut from when they first open through petal drop from a plant which will continuously yield cut flowers under greenhouse conditions.

The variety of rose plant of the present invention was obtained at Carlton, Ore. as a seedling from a floribunda variety seed parent entitled "Escort," U.S. Plant Pat. No. 2,436 and a pollen parent entitled "Golden Nugget," a non-patented, yellow floribunda rose variety grown in a limited amount in the greenhouse trade. The crossing was made in July 1981, the first seed of the crossing was sewn in March 1982 and the first flower appeared from these seedlings in May 1982.

Asexual reproduction of this new variety in Wasco, Calif. by means of budding shows that its unique characteristics come true to form and are established and transmitted through succeeding propagations through budding.

BRIEF DESCRIPTION OF THE DRAWINGS

In the accompanying drawings typical specimens of the vegetative growth and flowers of the new variety are shown in different stages of development and are depicted in color as nearly true as is reasonably possible to make in color illustrations of this character.

The top photograph depicts parts detached from the plant including, progressively, in the top row, flower stems (in side view) having, from left to right, petals removed, a receptacle split in cross section, a flower stem and receptacle with petals and stamens removed, a flower stem and bud as sepals are dividing, a flower stem and flower in half-open stage, and a face view of a flower in three-quarter-open stage. The bottom row depicts the top view of a five-leaflet leaf, the bottom view of a five-leaflet leaf, top and bottom views of detached petals, and a portion of a detached stem with foliage removed to depict thorns and stem coloration.

The bottom photograph shows a bouquet of flowers of Carale in various stages of opening.

DETAILED DESCRIPTION OF THE DISCLOSURE

The following description was made during November 1989 of rose plants of the new and distinct variety growing in a greenhouse at Carlton, Ore. Color designations are to *The Royal Horticulture Society Colour Chart.*

FLOWER

Flowers borne: Approximately 70% of the stems produce a single bloom and the remaining 30% are borne with two or three primary buds, two in pyramidal cluster on normal strength, medium length stems.

Quantity of bloom: Abundant in greenhouse.

Continuity: Continuous.

Fragrance: Moderate sweetbriar.

Bud:

*Peduncle.*—Medium length; medium weight; erect; medium green; medium roughness; medium prickles; green.

*Before calyx breaks.*—Size: medium. Form: medium length flat without foliaceous appendages on the surface of the bud.

*As calyx breaks.*—Color: Fan 3 Yellow-Green 144-A.

*As first petal opens.*—Size: medium. Form: medium length flat. Color: Outside: Fan 3 Yellow-Green 153-D. Inside: Fan 1 Yellow-Orange 14-B.

*Opening.*—It opens up well.

Bloom:

*Size when fully open.*—Medium, 3" to 3½".

*Petalage.*—From 32 to 35 petals; arranged regularly.

*Form.*—Cupped high centered; petals at first being loosely rolled outward; becoming later at maturity loosely rolled outward or flat.

Petals: Medium thickness; with inside satiny; outside satiny.

*Shape.*—Outer: obvate with single notch. Intermediate: obvate. Inner: ovate.

*Color.*—The yellow color of bloom intensifies from the sepals cracking stage, having a greenish cast, to a rich yellow at time of harvesting for florist use. Color of newly opened flowers: Outer petal: Outside surface: Fan 3 Yellow-Green 153-D. Inside surface: Fan 1 Yellow-Orange 14-B. Intermediate petal: Outside surface: Fan 1 Yellow-Orange 14-B. Inside surface: Fan 1 Yellow-Orange 12-A. Inner petal: Outside surface: Fan 1 Yellow-Orange 14-B. Inside surface: Fan 1 Yellow-Orange 12-A. Color of flower three days after opening: Outer petal: Outside surface: Fan 3 Yellow-Orange 153-D. Inside surface: Fan 1 Yellow-Orange 9-B. Inner petal: Outside surface: Fan 1 Yellow-Orange 14-B. Inside surface: Fan 1 Yellow-Orange 12-A.

General color effect:

*Newly open flower.*—A solid yellow color.

*Flowers three days open.*—A solid yellow color substantially the same as a newly opened flower; this color holds through to the spent bloom when placed in a vase or container and used as a cut flower.

Behavior: Petals persist; fading yellow — tips of petals fade to pale yellow in hot weather.

Flower longevity: On bush in garden 14 days in August; cut flowers grown outdoors kept at livingroom temperature 5 days in August; cut flowers grown in greenhouse kept at livingroom temperature 8 days in November.

REPRODUCTIVE ORGANS

Stamens: Many; arranged regularly about pistils.

*Filaments.*—Many; most with anthers; medium length.

*Color.*—Fan 1 16-A.

*Anthers.*—Open at various times; medium length. Color: Fan 1 21-A. An anther seldom fused with a petaloid.

*Pollen.*—Abundant; yellow-gold.

*Pistils.*—Medium number.

*Styles.*—Even; medium length; thin; bunched.

*Stigma.*—White.

*Ovaries.*—All enclosed in receptacle.

*Hips.*—Medium globular with inconspicuous neck; moderately prickly; walls thick; reddish.

*Sepals.*—Permanent; moderately long; spear-shaped, curled.

*Seeds.*—Medium number; medium size.

PLANT

Foliage:

*Leaves.*—Compound of three, five or seven leaflets; moderately abundant; medium size; normal five-leaflet leaf has an average length of 7 inches and an average width of 5 inches; moderately leathery.

*Leaflets.*—Ovoid with apex acute, base round, margin simply serratedentate.

*Color.*—Mature upper surface: Fan 3 139-A. Mature under surface: Fan 3 146-B. Young upper surface: Fan 3 141-A. Young under surface: Fan 3 143-A.

*Rachis.*—Medium. Upper side: grooved hairy. Under side: sparsely thorny.

*Stipules.*—Long; medium width; long points; turning out an angle of less than 90°.

*Disease.*—Resistance comparable to the average variety grown under the same cultural conditions.

Growth: Determined under greenhouse growing conditions; outdoor grown not determined as the variety is intended for greenhouse use.

*Habit.*—Upright, much branched.

*Growth.*—Very free, vigorous.

*Canes.*—Moderately heavy.

*Main stems.*—Bright. Color: Fan 3 141-B. Prickles: several. Color: Fan 4 185-B. Hairs: none.

*Branches.*—Bright. Color: Fan 3 141-C. Prickles: several. Color: Fan 4 180-B. Hairs: none.

*New shoots.*—Bright. Color: Fan 3 143-C. Prickles: several. Color: Fan 4 180-C. Hairs: none.

What is claimed is:

1. A new and distinct variety of rose plant of the floribunda class obtained as a seedling from a seed parent entitled "Escort" and a pollen parent entitled "Golden Nugget," characterized by its solid yellow color which is maintained from flower opening through petal drop, and its ability to yield flowers on a continuous basis when grown in a greenhouse, substantially as shown and described.

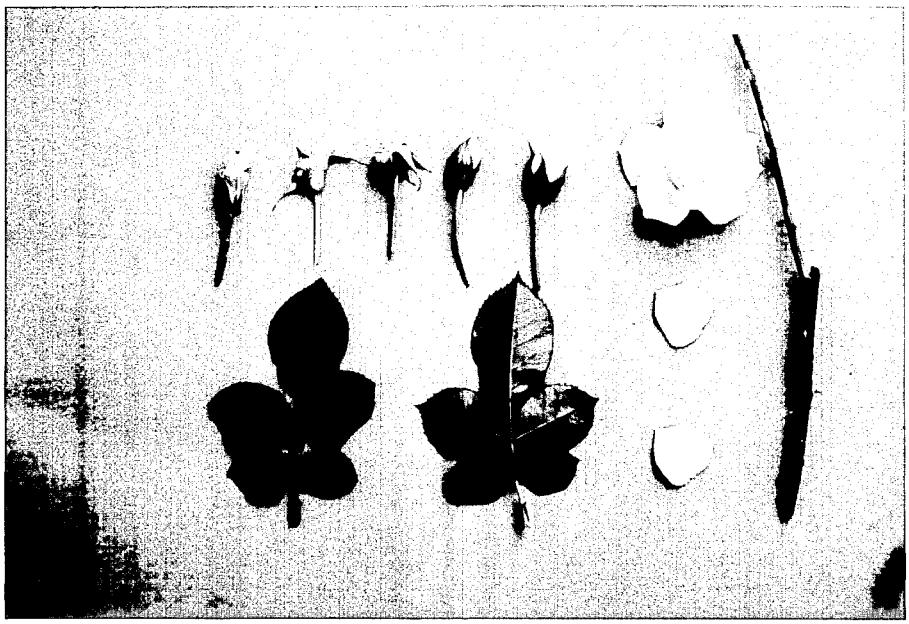
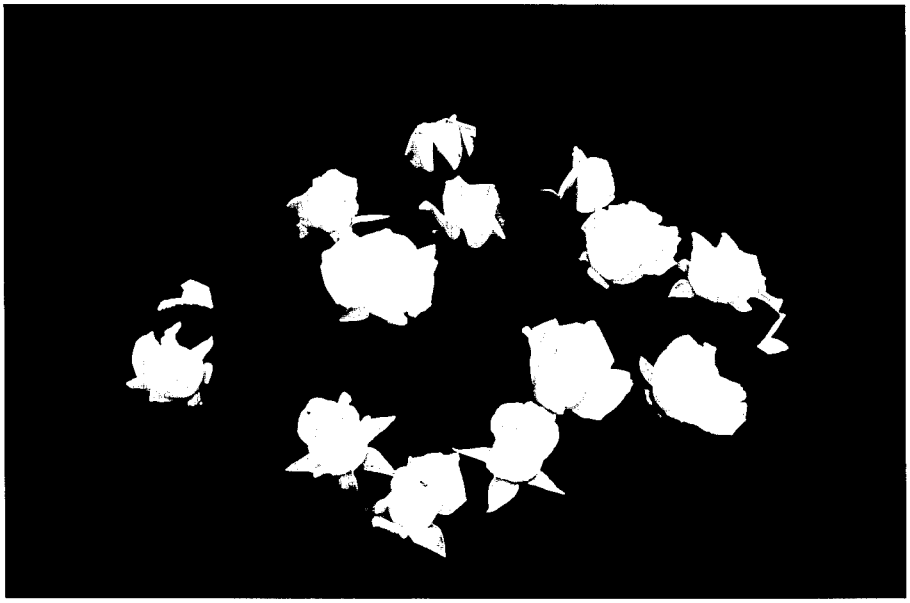

* * * * *